United States Patent [19]
Wiegand et al.

[11] Patent Number: 6,087,187
[45] Date of Patent: Jul. 11, 2000

[54] MASS-SENSITIVE BIOSENSORS

[75] Inventors: Andreas Wiegand, Schwalmstadt; Norbert Madry, Marburg; Carsten Schelp, Marburg; Paul Meller, Marburg; Michael Möhlen, Wehrshausen, all of Germany

[73] Assignee: Dade Behring Marburg GmbH, Marburg, Germany

[21] Appl. No.: 08/771,249

[22] Filed: Dec. 20, 1996

[30] Foreign Application Priority Data

Dec. 27, 1995 [DE] Germany ............... 195 48 376

[51] Int. Cl.[7] ............................................. G01N 33/553
[52] U.S. Cl. ............... 436/525; 435/4; 435/7.1; 436/501; 436/518; 436/524
[58] Field of Search ............ 435/4, 7.1; 436/518, 436/524, 525, 501

[56] References Cited

U.S. PATENT DOCUMENTS

| | | | |
|---|---|---|---|
| 4,236,893 | 12/1980 | Rice | 23/230 B |
| 4,735,906 | 4/1988 | Bastiaans | 436/527 |
| 5,314,830 | 5/1994 | Anderson et al. | 436/524 |

FOREIGN PATENT DOCUMENTS

| | | |
|---|---|---|
| 2160633 | 4/1996 | Canada . |
| 39 20 052 | 1/1991 | Germany . |
| 44 36 910 | 4/1996 | Germany . |

OTHER PUBLICATIONS

Kenneth A. Davis and T. Richard Leary, "Continuous Liquid–Phase Piezoelectric Biosensor for Kinetic Immunoassays," *Analytical Chemistry*, 61, No. 11, Jun. 1, 1989, pp. 1227–1230.

Ebersole, Richard C. and Ward, Michael D., "Amplified Mass Immunosorbent Assay with a Quartz Crystal Microbalance," *Journal of the American Chemical Society*, vol. 110, Nr. 26, pp. 8623–8628 (1988).

Dickert and Schuster, "Piezoelektrische Chemosensoren– von der Adsorption zur molekularen Erkennung mit Wirt– Gast–Chemie," *Chemie in unserer Zeit*, 28(3):147–152 (1994).

Carter et al., *Analytical Letters*, 28(8) 1379–1386, Jun. 1995.

Plomer et al., *Enzyme Microb. Technol.* 14:230–235, Mar. 1992.

*Primary Examiner*—Robert D. Budens
*Assistant Examiner*—Territa Gray
*Attorney, Agent, or Firm*—Finnegan, Henderson, Farabow, Garrett & Dunner, L.L.P.

[57] ABSTRACT

The present invention relates to a piezoelectric sensor for use in diagnostic and analytic processes, in particular for the immunochemical detection of diagnostically relevant specific binding partners.

15 Claims, No Drawings

MASS-SENSITIVE BIOSENSORS

The present invention relates to a piezoelectric sensor for use in diagnostic and analytic processes, in particular for the immunochemical detection of diagnostically relevant specific binding partners.

Piezoelectric sensors as such are known, for example, from Dickert et al. (Chemie in unserer Zeit [Chemistry Today] 28 (3), pp. 147–152 (1994)). Such biosensors are, for example, also described in U.S. Pat. Nos. 4,236,893 and 4,735,906.

Such biosensors, which can be used for the detection of diagnostically relevant molecules (analytes), generally consist of a transducer having a surface which is coated with a binding partner specific to the molecule to be detected and therefore capable of selectively binding these molecules. Piezoelectric quartz crystals are usually used as the transducer. If the quartz crystal is built into a corresponding electronic circuit, then it oscillates at a particular resonant frequency. If the molecules to be detected then accumulate, then the resonant frequency is shifted. Such electronic circuits are known to the person skilled in the art, for example from DE-A 39 20 052.

These known biosensors already partly achieve the stated aims. However, it is found that, with the processes employed, in which, for example, antibodies are bound by silane derivatives to the quartz surface, on the one hand the process for binding the antibodies to the quartz surface is very elaborate and poorly reproducible and, on the other hand, the process for making the sensor surface reusable, by treatment with a reagent solution which is intended to break the binding between the antigen to be detected and the antibody, and to separate the bound antigen, is for its part poorly reproducible and leads to uncontrolled breakdown of the antibodies on the sensor surface.

A publication by Davis et al. (Anal.Chem. (1989), 61 (11), pp.1227–1230) describes that it is possible to coat the transducer with gold and bind protein A to this layer. For its part, protein A can reversibly bind antibodies for the detection of diagnostically relevant molecules. As the authors themselves explain, the protein A coating strongly shifts the signal and overall hinders the measurement.

The object of the present invention is therefore to propose a biosensor for use in analytic or diagnostic processes, which is simple to coat with a specific binding partner and at the same time can be regenerated simply and reliably after the specific reaction has taken place.

According to the present invention, this object is achieved by coating the sensor with a precious metal, preferably gold, and a specific binding partner can be bound to this coating. The specific binding partner can be separated from the biosensor thus coated, for example using the reagents disclosed by DE 44 36 910.

The embodiment of the transducer or the manner in which the change due to the accumulation of analytes is converted into a measurement signal are not essential for the present invention. The present invention can be used in both manual processes, in which, for example, the sensor is dipped onto the sample, and in automatic analysis machines.

In principle, the process according to the invention can be implemented as follows: a commercially available gold-coated piezoelectric crystal, which is integrated into a suitable electronic circuit (for example from the company Sensotec) is coated with a binding partner specific to the analyte to be determined. Such a specific binding partner may, for example, be a monoclonal or polyclonal antibody or antibody fragment, a lectin or an antigen. The coating time may be between 5 min and several hours, preferably between 10 and 120 min. After coating, the sensor surface is rinsed with washing buffer. The washing buffer preferably contains a detergent. The specific coating may optionally be followed by a further non-specific coating, for example with BSA or inactivated POD, in order to prevent non-specific binding. Such processes are known per se to the person skilled in the art. A washing step may also take place after such a subsequent non-specific coating.

The coated sensor is incubated with the sample, it being possible for this to take place, for example, by dipping into the sample or by application of a sample onto the sensor surface. A further advantageous embodiment is one in which the sensor surface is designed in such a way that measurements can be taken under continuous flow conditions. It is easy for the person skilled in the art to decide which design the respective sensor must have according to its application.

As a result of the reaction of the analyte with the specific binding partner, the measured quantity, for example the resonant frequency, determined by the electronic circuit is shifted. The amount of analyte bound can be deduced from the change in the measured quantity, for example by comparison with a reference curve. The arrangement is also suitable for being calibrated directly in mass units. In order to determine the change in the measured quantity, it is possible, for example, to use a reference electrode which is not coated with the specific binding partner. Advantageously, a further washing step takes place after the end of the incubation with the sample. The incubation with the sample may advantageously take place between 1 and 100 min, particularly advantageously between 5 and 60 min, and most advantageously between 10 and 30 min.

The regeneration may take place as described in DE 44 36 910. In this case, when precious metals, preferably gold, are employed as the solid phase, particular reducing or oxidizing agents such as, for example, sodium borohydride or tetrabutylammonium hydroxide are used for the regeneration, with or without the addition of detergents.

The following illustrative embodiment is intended to explain the invention without placing any restriction on it.

EXAMPLE

Quantitative Human IgE Determination

Support:
Gold coated piezoelectric crystal from the company Sensotec framed in a Teflon ring (external diameter 36 mm). Gold surface diameter: 9 mm gold surface area: 14 mm$^2$.

Coating:
50 μl of a polyclonal antibody (rabbit) against human IgE are applied to the sensor. The concentration of the Ab is 5 μg/ml. The solution furthermore contains 75 mM Na phosphate, 75 mM NaCl, 100 g/l Na$_2$SO$_4$. The pH is 6.0. The Ab solution is left for 1 hour at 37° C. or overnight at room temperature.

Washing Step:
The supernatant is removed and the sensor is rinsed 5 times with 250 μl of washing buffer in each case. The washing buffer consists of a solution of 50 mM tris (hydroxymethyl)aminoethane (TRIS) and 50 mM of citric acid, pH 7.4.

Subsequent Coating:
50 μl of inactivated peroxidase (POD) are applied to the sensor. The POD concentration is 1 g/l. The solution furthermore contains 75 mM Na phosphate, 75 mM NaCl, 100 g/l Na$_2$SO$_4$. The pH is 6.0. The POD solution is left for one hour at 37° C. or overnight at room temperature.

Washing Step:

The supernatant is removed and the sensor is rinsed 5 times with 250 μl of washing buffer in each case. The washing buffer consists of a solution of 50 mM tris (hydroxymethyl)aminoethane (TRIS) and 50 mM of citric acid, pH 7.4.

Sample Incubation:

50 μl of human serum containing defined quantities of IgE are applied to the sensor and incubated for 30 min at 37° C.

Washing Step:

The supernatant is removed and the sensor is rinsed 5 times with 250 μl of washing buffer (5 mM Na phosphate, 85 mM NaCl, 1 g/l Tween 20, 0.5 g/l phenol, pH 6.5).

Regeneration of the Solid Phase:

250 μl of a 20% (% by weight) tetrabutylammonium hydroxide solution are applied to the sensor and incubated for 1 hour at 37° C.

Washing Step:

After removal of the supernatant, the sensor is rinsed 5 times with deionized water.

2nd Regeneration:

250 μl of 1% (% by weight) $NaBH_4$ solution are incubated for 15 min at room temperature on the sensor. The solution furthermore contains 50 mM of 2-(cyclo-hexamino) ethanesulfonic acid (CHES). The pH is 10.0.

Washing Step:

After removal of the supernatant, the sensor is rinsed three times with deionized water and three times with a phosphate-buffered saline solution (pH 7.2).

Results*

1. Determination with 100 IU/ml human IgE=829 aU**
2. Determination with 100 IU/ml human IgE=576 aU
3. Determination with 100 IU/ml human IgE=623 aU
4. Determination with 0 IU/ml human IgE=19 aU
5. Determination with 100 IU/ml human IgE=767 aU
6. Determination with 100 IU/ml human IgE (Control= nonspecific coating antibody)=14 aU

* Average of n=2
** Arbitrary units

We claim:

1. A process for the immunochemical detection of an analyte in a sample of a biological fluid, comprising:

directly binding a first specific binding partner to a solid phase, the solid phase being a piezoelectric sensor coated with a precious metal, incubating the bound, coated sensor with a sample, detecting the presence of an analyte in the sample, and regenerating the solid phase by separating the first specific binding partner from the solid phase by treatment with a suitable reagent containing a reducing or oxidizing agent.

2. The process as claimed in claim 1, wherein the first specific binding partner is an immunoglobulin or an antigen-binding fragment thereof.

3. The process as claimed in claim 1, wherein the reagent contains $NaBH_4$.

4. The process as claimed in claim 1, wherein the reagent contains tetrabutylammonium hydroxide.

5. The process of claim 1, wherein the precious metal is gold.

6. The process of claim 1, wherein the reagent is a reducing agent.

7. The process of claim 1, wherein the reagent is an oxidizing agent.

8. The process of claim 1, wherein the detecting step further comprises quantitating the amount of analyte in the sample.

9. The process of claim 1, wherein the incubating step is selected from the group consisting of dipping the sensor into the sample, applying the sample onto the sensor surface, and passing the sample across the sensor under continuous flow conditions.

10. The process of claim 1, wherein the process further comprises washing the sensor after directly binding the first specific binding partner to the solid phase.

11. The process of claim 1, wherein the process further comprises binding of a non-specific coating to the solid phase after binding the first specific binding partner to the solid phase.

12. The process of claim 11, wherein the process further comprises washing the sensor after binding of the non-specific coating.

13. The process of claim 1, wherein the first specific binding partner is a lectin or an antigen.

14. The process of claim 2, wherein the immunoglobulin is a polyclonal antibody or the antigen-binding fragment is a fragment of a polyclonal antibody.

15. The process of claim 2, wherein the immunoglobulin is a monoclonal antibody or the antigen-binding fragment is a fragment of a monoclonal antibody.

* * * * *